(12) United States Patent
Fulston et al.

(10) Patent No.: US 6,573,074 B2
(45) Date of Patent: Jun. 3, 2003

(54) METHODS FOR ANSAMITOCIN PRODUCTION

(75) Inventors: Mark Fulston, Redhill (GB); Anna L. Stefanska, Barley (GB); Jan E. Thirkettle, Shoreham-by-Sea (GB)

(73) Assignee: SmithKline Beecham plc, Brentford (GB)

(*) Notice: Subject to any disclaimer, the term of this patent is extended or adjusted under 35 U.S.C. 154(b) by 0 days.

(21) Appl. No.: 09/828,758

(22) Filed: Apr. 9, 2001

(65) Prior Publication Data

US 2002/0015984 A1 Feb. 7, 2002

Related U.S. Application Data

(60) Provisional application No. 60/196,361, filed on Apr. 12, 2000.

(51) Int. Cl.⁷ .......................... C12P 21/04; C12P 17/18; C12P 17/14
(52) U.S. Cl. ..................... 435/119; 435/120; 435/71.1
(58) Field of Search .............................. 435/120, 71.1, 435/119

(56) References Cited

U.S. PATENT DOCUMENTS

| | | | |
|---|---|---|---|
| 3,929,992 A | 12/1975 | Surendra et al. | 424/122 |
| 4,162,940 A | 7/1979 | Higashide et al. | 435/119 |
| 4,228,239 A | 10/1980 | Higashide et al. | 435/119 |
| 4,356,265 A | 10/1982 | Hatano et al. | 435/119 |
| 4,450,234 A | 5/1984 | Hasegawa et al. | 435/253 |
| 5,208,020 A | 5/1993 | Chari et al. | 424/85.91 |

FOREIGN PATENT DOCUMENTS

| | | |
|---|---|---|
| EP | 0 019 934 A | 12/1980 |
| EP | 0 026 338 A | 4/1981 |
| EP | 0 031 430 A | 7/1981 |
| GB | 1 554 395 A | 10/1979 |
| WO | WO91/09134 A | 6/1991 |

*Primary Examiner*—Herbert J. Lilling
(74) *Attorney, Agent, or Firm*—Andrea V. Lockenour; Elizabeth J. Hecht; Edward R. Gimmi

(57) ABSTRACT

Improved purification methods for ansamitocins are disclosed.

13 Claims, No Drawings

METHODS FOR ANSAMITOCIN PRODUCTION

This application claims the benefit of Provisional application 60/196,361, filed Apr. 12, 2000.

FIELD OF THE INVENTION

This invention relates to processes for the preparation of ansamitocins, in particular ansamitocins which can be converted to maytansinol.

BACKGROUND OF THE INVENTION

Highly cytotoxic maytansinoid drugs and their therapeutic use have been described in U.S. Pat. No. 5,208,020. These drugs can be prepared from ansamitocin precursors produced by fermentation of microorganisms such as Actinosynnema.

Under defined culture conditions, Actinosynnema spp. such as Actinosynnema pretiosum produce a number of related ansamitocins. The major product is ansamitocin P-3 with an isobutyryl moiety at the C-3 position. Other ansamitocins differing only in the C-3 acyl side chain are produced as minor components, P-1 (ethionyl moiety), P-2 (propionyl moiety), P-3' (butyryl moiety), P-4 (isovaleryl moiety) and P-4' (valeryl moiety). All these compounds may undergo reductive cleavage to produce a common product, maytansinol (form P-0). In addition, a number of other ansamitocins are produced at low levels, which are modified at other sites in the molecule (hydroxylated or n-demethylated). These do not produce the desired P-0 on deacylation.

Processes for ansamitocin P-3 production from Actinosynemma spp. have been described in U.S. Pat. Nos. 4,162,940; 4,228,239; 4,356,265; and 4,450,234. In general, these methods require adding a filter aid and a water-miscible solvent to whole fermentation broth, removing solids and extracting the aqueous fraction with a water-immiscible solvent, concentrating and precipitating with petroleum ether, purifying the precipitate using silica chromatography, and crystallizing followed by further chromatography or re-crystallization. Alternative processes utilize Diaion HP-10 adsorption instead of silica chromatography followed by further solvent extraction and crystallization.

These processes can be used to gain acceptable yields of ansamitocin P-3, but the methods involve a large number of stages which introduce limitations in large-scale production operations, particularly because of the extremely toxic nature of the ansamitocin compounds and the necessity of ensuring the safety of the human operators of the processes. Thus, a need exists to have a safer alternative procedure available, utilizing fewer and more contained stages.

SUMMARY OF THE INVENTION

One aspect of the present invention is a method for preparing purified ansamitocins comprising the steps of:

a. culturing an ansamitocin-producing microorganism in a liquid culture medium;

b. treating the culture medium to facilitate solvent extaction of ansamitocins;

c. extracting ansamitocins from the culture medium with an aromatic hydrocarbon solvent;

e. concentrating the extracted ansamitocins; and f. purifying the ansamitocins by crystallization.

Another aspect of the present invention is a method for preparing purified ansamitocins comprising the steps of:

a. culturing an ansamitocin-producing microorganism in a liquid culture medium;

b. extracting ansamitocins from the culture medium with an aromatic hydrocarbon solvent;

c. concentrating the extracted ansamitocins; and d. purifying the ansamitocins by crystallization.

DETAILED DESCRIPTION OF THE INVENTION

All publications, including but not limited to patents and patent applications, cited in this specification are herein incorporated by reference as though fully set forth.

Methods are provided for preparing purified ansamitocins without a filtration step. The methods comprise the steps of culturing an ansamitocin-producing microorganism in a liquid culture medium, treating the culture medium to release ansamitocins from the microorganism into the culture medium thereby facilitating solvent extraction, extracting ansamitocins from the treated culture medium with an aromatic hydrocarbon solvent, concentrating the extracted ansamitocins, and purifying the ansamitocins by crystallization. Alternatively, the treatment step can be omitted.

The purified ansamitocins may be reduced to maytansinol and include ansamitocin P-3, P-1, P-2, P-3', P-4 and P-4'. The purified ansamitocins contain only very low levels of undesirable ansamitocins with modifications at other sites in the molecule. Preferably, the ansamitocin-producing microorganism is Actinosynnema spp. Particularly preferred is *Actinosynnema pretiosum* ATCC 31565. Also particularly preferred is *Actinosynnema pretiosum* ATCC 31281. The microorganisms can be grown by fermentation culture techniques well-known to those skilled in the art such as those disclosed in U.S. Pat. No. 4,450,234.

One embodiment of the method of the invention uses treatment of the microorganism to aid release of intracellular ansamitocins and render cell-associated ansamitocins more amenable to solvent extraction. Exemplary treatment methods include sonication, increased pressure or increased temperature. Preferably, the treatment is a heat treatment. The heat treatment can be conducted at about 60° C. to about 80° C. Preferably, the heat treatment step is conducted at about 75° C. which kills the microorganism and facilitates solvent extraction of ansamitocins. In an alternative embodiment, no treatment step is used prior to extraction since approximately 60% of total ansamitocins can be found in the culture medium.

Ansamitocins can be extracted from culture medium with the use of aromatic hydrocarbon solvents. The aromatic hydrocarbons have a particular selectivity for the ansamitocins over other broth constituents, which ensures only simple processes are required downstream to isolate pure product. Preferably, the aromatic hydrocarbon solvent is toluene or xylene. Particularly preferred is toluene as this is more amenable to low temperature evaporation. The properties of toluene and xylene are such that the solvent and aqueous layers are readily separated under gravity without the need for mechanical separation and thus greater containment of the process and increased operator safety are achieved. The extraction can be conducted at about 20° C. to about 60° C. Preferably, the extraction is conducted at about 45° C. The pH of the aqueous solution prior to extraction should be in the range 3 to 9. Preferably, the pH is near neutrality, i.e., pH 6 to 8.

In general, one equivalent volume of solvent to whole broth (1:1) is preferred for the extraction. Alternative ratio ranges of 2:1 to 1:4 can also be used. The solutions are generally mixed slowly with stirring and the mixture stirred until about >80% of the ansamitocins have been extracted into the organic layer. Preferably the mixture is left to settle under gravity at a temperature between 15° C. and 50° C. The preferred temperature for settling is about 45° C.

The organic layer is removed, and concentration of the extract by volume reduction of the solvent may be carried out in vacuo or by other methods well-known to those skilled in the art. After volume reduction, the concentrated extract can be optionally dissolved in a polar solvent such as methanol, and clarified using a membrane filter such as PTFE, or a depth filter such as silica or alumina.

Crystallization is used to purify the desired ansamitocins, particularly P-3, by reducing the levels of unwanted ansamitocins. A preferred solvent mixture for crystallization is ethyl acetate and heptane. Such crystallization is performed in a conventional manner. To aid dissolution of the solid for crystallization, a small volume of methanol or similar polar solvent may be added prior to addition of ethyl acetate and then treatment with larger volumes of heptane, optionally with stirring and cooling to afford the crystallized product. The product may be recrystallized following the same procedure.

Alternatively, prior to crystallization, the impure ansamitocins extracted from the fermentation broth may be purified using silica gel, e.g., by passing a solution of the solvent extract through a bed of silica. Solvents used for the chromatography may be toluene and toluene-methanol mixes. Other solvents known to those skilled in the art can also be used. The fractions containing ansamitocin P-3 are pooled and concentrated under reduced pressure.

Methods are also provided for analysis of ansamitocins by HPLC. Quantitation of ansamitocin P-3 and analysis of ansamitocin ratios are achieved by the methods. These methods were employed in the Examples set forth below.

Quantitation of ansamitocin P-3 in broth and extraction samples can be determined on a C18 Waters Q Spherisorb S5 ODS2 column, 4.6×250 mm, with a 10 mm guard column. UV detection is at 252 nm and 205 nm. An isocratic mobile phase of 1 ml/min 60% MeCN (0.05% TFA) in water (0.05% TFA) and a 20 µl injection volume are used.

Analysis of ansamitocin ratios in downstream process samples can be determined on a C8 Waters Symmetry Shield column, 3.9×150 mm, with no guard column. UV detection is at 252 nm and 205 nm. A gradient mobile phase of 1 ml/min 35–45% MeCN (0.05% TFA) in water (0.05% TFA) over 30 minutes with a 10 minute re-equilibration at 40° C. and a 10 µl injection volume are used.

Analysis of ansamitocin ratios in chromatography fractions and final product can be determined on a C8 Waters Symmetry Shield column, 3.9×150 mm, with no guard column with an LC-MS detection system, atmospheric pressure electrospray ionisation, +ve ion mode. 30 V cone voltage Mass detection to positively identify the peaks is achieved by full scan MS (scan from 600–700 amu with quad 1). MS-MS fragmentation to determine class of ansamitocin is carried out using the same gradient system. A gradient mobile phase of 1 ml/min 35–45% MeCN (0.05% TFA) in water (0.05% TFA) over 30 minutes with a 10 minute re-equilibration at 40° C. and a 10 µl injection volume are used.

Quantitation of ansamitocin P-3 in waste streams and other low-level samples requiring high sensitivity can be determined on a C18 Waters Spherisorb S5 ODS2 column, 4.6×250 mm, with a 10 mm guard column and LC-MS-MS atmospheric pressure electrospray ionisation detection system, +ve ion mode, 30 V cone voltage. For determination of structural type, the molecular ions of the major species were selected and the fragmentation patterns observed were a predominant 547 ion indicating N-methylated and a 533 indicating N-demethylated. An isocratic mobile phase of 1 ml/min 60% MeCN (0.05% TFA) in water (0.05% TFA) and a 20 µl injection volume are used.

The process of the invention can be used to make cell-binding agent/maytansinoid complexes which are useful as tumor-activated pro-drugs. Ansamitocins prepared by the process of the invention can undergo reductive cleavage to maytansinol which can be used as described in U.S. Pat. No. 5,208,020 to produce N-methyl-L-alanine containing maytansinoid derivatives. These derivatives are then conjugated to cell-binding agents, preferably antibodies, via various linkers such as a disulfide link.

An exemplary cell-binding agent/maytansinoid complex can be prepared by a process comprising the following steps:
(1) reducing ansamitocins prepared by the process of the invention to maytansinol;
(2) esterifying maytansinol with N-methyl-L-alanine derivatives to form a disulfide-containing maytansinoid ester;
(3) reducing the disulfide-containing maytansinoid ester prepared by step (2) to a thiol-containing maytansinoid;
(4) introducing dithiopyridyl groups into a cell-binding agent; and
(5) linking the thiol-containing maytansinoid produced by step (3) to the dithiopyridyl cell-binding agent of step (4) by a disulfide link.

The present invention will now be described with reference to the following specific, non-limiting examples.

EXAMPLE 1

Extraction of *Actinosynnema pretiosum* Culture Broth and Ansamitocin Purification 37 L of whole broth containing the producing strain *Actinosynnema pretiosum* ATCC 31565 (ansamitocin P-3 titer 86.3 mg/L) were heat-treated in situ at 75° C. for 60 mins to kill the micro-organism and facilitate solvent extraction of the ansamitocins. 40 L of toluene were added and the mixture warmed to 45° C. Phases were agitated such that a vortex of upper toluene phase was drawn into the lower broth phase but without emulsification or complete homogenisation of the phases. Extraction was completed within 16 hours, and separation under gravity within 2 hours.

39 L of toluene containing 80 mg/L P-3 was recovered by siphon, and evaporated using a 20 L rotary evaporator (bath temperature 40–45° C., rate ~9 L/hr). 11.2 g of mobile oil, containing 3.1 g of P-3; 27.6% w/w) was generated after evaporation. The resulting extract was transferred to a flask by dissolution in toluene and re-evaporation. (Extraction stage yield=97%)

The extract was taken up in 120 ml toluene and loaded onto a silica column (Kieselgel 60, 125 ml bed volume packed in toluene, 4 cm diam. ×10 cm) in 375 ml toluene (3 bv). The column was washed with 2 bv toluene and then eluted with 4×2 bv of 2% MeOH in toluene, followed by 12×1 bv of 4% MeOH in toluene. The column was eluted at 40 ml/min and produced tight bands of color. Fractions 7–10 containing ansamitocin P-3 were bulked and evaporated to produce 3.2 g of oily solid containing 2.5 g of P-3. This material was analyzed by LC-MS and MS-MS.

At this stage the product contained 85.1% ansamitocin P-3, and a total of 93.9% of the desired ansamitocins. (Column stage yield=80.6%)

The product from the silica column was taken up in 200 mL EtOAc warmed to 40° C. Heptane (200 mL) was added and the solution allowed to cool. The solution was seeded with 1mg pure P-3 crystals (crystallization also spontaneously occurred at other sites in the flask). After 4 hours at ambient temperature the supernatant was analyzed by HPLC and 0.8 g P-3 (30%) was determined to still be in solution. Further heptane was added (150 ml) and the flask left for a further 3 hours and re-analysed. This indicated that 0.4 g of P-3 (16%) remained in solution. The flask was left overnight at 4° C. Subsequent analysis indicated that only 70 mg of P-3 (3%) remained in solution. The mother liquors were removed by aspiration, using a sintered filter line assembly. The white needle crystals were washed with 2×15 mL 1:3 EtOAc:heptane. The crystals were dried in situ under vacuum on a rotary evaporator at 30° C. for 10 hours. 2.5 g of crystals were obtained. (Crystallization yield=86%)

The final product contained 86% ansamitocin P-3, and a total of 98.4% of the desired acylated ansamitocins (P-1, P-2, P-3, P-3', P-4, P-4').

EXAMPLE 2
Extraction of *Actinosynnema pretiosum* Culture Broth and Ansamitocin Purification 1,100 L of whole broth containing the producing strain *Actinosynnema pretiosum* ATCC 31565 (ansamitocin P-3 titer 75.1 mg/L, 82.6 g P-3) were heat-treated in situ at 75° C. for 60 mins to kill the microorganism and facilitate solvent extraction of the ansamitocins. 77.6 g of P-3 remained after the heat kill process. An equal volume of toluene pre-warmed to 45° C. was added and the mixture was maintained at 45° C. Phases were agitated such that a vortex of upper toluene phase was drawn into the lower broth phase but without emulsification or complete homogenization of the phases. Extraction was carried out for 45 hours, followed by separation under gravity which occurred within 30 min. (Extraction stage yield 90.3%.)

1,127 L of the toluene extract, containing the ansamitocins, were concentrated to 22 L using a falling film evaporator (FFE). The concentrate was transferred to a 50 L rotary evaporator and evaporated to low volume (evaporation rate 14.6 L/hr). The FFE was rinsed with 2×20 L toluene and the rinsings passed to the evaporator to ensure complete transfer of product. The concentrate was evaporated to dryness.

The dry extract was taken up in 7.2 L of 4% methanol in toluene and loaded onto a silica column (Kieselgel 60, 4.8 L bed volume packed in 4% methanol in toluene, 15.0 cm diam. ×27.0 cm, loading rate 120 mL/min). The column was eluted isocratically using 4% methanol in toluene at a flow rate of 227–384 mL/min and produced tight bands of color. Initial fractions were one bed volume; fractions 3 to 6 were collected as half bed volumes. Fractions were monitored by TLC (Kieselgel 60 $F_{254}$ plates, run in 5% methanol in dichloromethane, visualized by UV at 254 nm) and those containing ansamitocins were monitored by HPLC and LC-MS. Fraction selection for crystallization was based on HPLC and LC-MS analysis of the fractions to optimize ansamitocin P-3 recovery and minimize undesired ansamitocins. Fractions 5 to 10 containing ansamitocin P-3 were bulked and evaporated to produce a solid containing 54.6 g of P-3. At this stage the product contained 77.1% ansamitocin P-3, and a total of 96.1% of the desired acylated ansamitocins. (Column stage yield=92.5%)

The product from the silica column was taken up in 91 mL methanol previously warmed to 46° C., followed by 546 mL ethyl acetate warmed to the same temperature. Further aliquots of methanol were added to aid dissolution of the solid. A total of 166 mL of methanol was added to the mixture. Heptane (100 mL) warmed to 50° C. was added to the first sign of cloudiness and then the solution was allowed to cool to ambient as crystallization commenced. After 4 hours, a further 1,324 mL of heptane (at ambient temperature) was added. The supernatant was analyzed by HPLC and 6.6 g P-3 was determined to still be in solution. The mixture was cooled on ice and further aliquots of heptane (200 and 400 mL) were added until 3.9 g of P-3 (6.8%) remained in the mother liquor.

The mother liquors were removed by aspiration, using a sintered filter line assembly. The crystals were washed with 2×150 mL 1:3 ethyl acetate:heptane. The crystals were dried in situ on a rotary evaporator, initially under low vacuum, followed by high vacuum (1.0–1.3 mbar) at 30° C. for 88.5 hours. 76.4 g of crystals were obtained.

The final product contained 74.5% ansamitocin P-3 (56.9 g) and a total of 97.8% of the desired acylated ansamitocins. (Overall yield=69%)

EXAMPLE 3
Silica Chromatography and Crystallization of the Ansamitocins 1,008 L of Actinosynnema pretiosum whole broth with a titer of 64.8 mg/L ansamitocin P-3 were heat treated, extracted with toluene and evaporated essentially as described in Example 1.

The concentrate containing 34.5 g ansamitocin P-3 was taken up in 3 L toluene and loaded onto a silica column (Kieselgel 60, 3.0 L bed volume, packed in toluene, 13.8 cm diam. ×16.6 cm). The column was topped with a 4 cm bed of sand. The column was washed with 5 L of toluene, followed by 20 L of 2% MeOH in toluene, which was collected as 5 L fractions. The column was then eluted with 20 L of 4% MeOH in toluene, collected as 2.5 L fractions. The ansamitocins were eluted in fractions 9 through to 15. Fraction selection for crystallization was based on HPLC and LC-MS analysis of the fractions to optimize ansamitocin P-3 recovery and minimize undesired ansamitocins. Fractions 10 to 12 were bulked and evaporated to dryness to yield an oil containing 32.5 g of ansamitocin P-3.

At this stage the product contained 91.8% ansamitocin P-3, and a total of 95.3% of the desired acylated ansamitocins. (Column stage yield=94.2%)

The concentrate from the bulked silica fractions, was warmed in a water bath at 50° C. and dissolved in a minimum volume of warm methanol/ethyl acetate (50° C.). 60 mL of methanol was added initially, followed by slow addition of 300 mL of ethyl acetate. A further 20 mL of warm methanol was added at which point the concentrate was completely dissolved. 200 mL of warm heptane (50° C.) was added and the crystallization solution removed from the water bath. Crystallization commenced, and further heptane was added in 200 mL aliquots until a total volume of 800 mL had been added. The mixture was cooled in an ice bath for 18 hours. The crystallization was monitored by HPLC analysis of the mother liquors. At 18 hours 6.3% ansamitocin P-3 remained in the mother liquors. A further 200 mL of heptane was added and the mixture cooled for a further five hours. HPLC analysis indicated 4.0% ansamitocins remained in the mother liquors.

The crystals were recovered by aspiration of the dark brown mother liquors. The crystals were washed three times with 50 ml of heptane:ethyl acetate, 3:1 and were dried under vacuum (0.8 mBar) overnight. The crystals were uniform, fine, off-white needles containing 28.2 g of ansamitocin P-3. (Crystallization stage recovery=86.9%)

The final product contained 93.1% ansamitocin P-3 and a total of 98.4% desired acylated ansamitocins.

EXAMPLE 4
Purification and Crystallization of Ansamitocins from Toluene Extract 1,001 L of Actinosynnema pretiosum whole broth with a titer of 74.5 mg/L ansamitocin P-3 were heat treated, extracted with toluene and evaporated essentially as described in Example 1 to give 9.5 L of concentrated extract containing 54.7 g of ansamitocin P-3.

The concentrate was heated to 45° C. and 14.5 L of heptane was added over 33 min to precipitate the ansamitocins. The mixture was cooled on ice. A further 5 L of heptane was added and the mixture allowed to settle overnight. The mother liquor was removed by aspiration and the precipitate was washed with 10 L of toluene:heptane, 1:1. HPLC analysis indicated the mother liquor contained 6.5% of ansamitocin P-3, and the wash contained 1.8% P-3. The precipitate was dissolved in 2 L of methanol and filtered through a 0.2 micron filter.

The methanol solution was evaporated to dryness and re-dissolved in 85 mL of methanol at 50° C. 510 mL of ethyl acetate was added to the solution followed by 200 mL of heptane. The mixture was cooled to ambient and a further 990 mL of heptane was slowly added as crystallisation commenced. 4.14 g of ansamitocin P-3 remained in the mother liquor. A further 400 mL of heptane was added and the mixture cooled on ice. 2.7 g of ansamitocin P-3 remained in the mother liquor.

The mother liquor was removed by aspiration and the crystals were dissolved in 110 mL of methanol and 520 mL ethyl acetate at 50° C. Heptane was added in two 75 mL aliquots, the mixture was cooled to ambient and another 900 mL added. A further 400 mL of heptane was added and the mixture cooled on ice and left overnight to crystallize. HPLC analysis indicated 2.3 g of ansamitocin P-3 remained in the mother liquor. The mother liquor was removed by aspiration and the crystals were washed with heptane:ethyl acetate, 3:1 and were dried under vacuum (0.6 mBar) overnight. The 47.8 g of crystals contained 84.3% ansamitocin P-3, and a total of 97.0% desired acylated ansamitocins.

EXAMPLE 5
Extraction of *Actinosynnema pretosium* Culture Broth with Xylene and Ansamitocin Purification 220 mL of heat treated Actinosynnema pretiosum, with a titre of 44 ug/ml ansamitocin P-3, were placed in a 45° C. water bath and an equal volume of xylene was added. The phases were mixed such that a vortex of xylene was drawn in to the lower broth phase but without forming an emulsion. After 20 hours, 64% of the ansamitocin P-3 had extracted into the xylene phase.

The mixture was separated under gravity and 170 mL of xylene were removed. The xylene extract was evaporated to dryness. The xylene extract was purified using silica chromatography. The extract was dissolved in 2 mL of 4% methanol in toluene and loaded and eluted using the same solvent mix. Fractions (0.5 mL) were collected and assayed by TLC (Kieselgel 60 $F_{254}$ plates run in dichloromethane:methanol 20:1). Fractions containing ansamitocin P-3 were crystallized using the procedure described in previous examples. The crystalline product was of comparable quality in terms of colour and purity with that produced by toluene extraction of fermentation broth.

The present invention may be embodied in other specific forms without departing from the spirit or essential attributes thereof, and, accordingly, reference should be made to the appended claims, rather than to the foregoing specification, as indicating the scope of the invention.

What is claimed is:

1. A method for preparing purified ansamitocins comprising the steps of:
   a. culturing an ansamitocin-producing microorganism in a liquid culture medium;
   b. treating the culture medium to facilitate solvent extraction of ansamitocins;
   c. extracting ansamitocins from the culture medium with an aromatic hydrocarbon solvent;
   d. concentrating the extracted ansamitocins; and
   e. purifying the ansamitocins by crystallization.

2. A method for preparing purified ansamitocins comprising the steps of:
   a. culturing an ansamitocin-producing microorganism in a liquid culture medium;
   b. extracting ansamitocins from the culture medium with an aromatic hydrocarbon solvent;
   c. concentrating the extracted ansamitocins; and
   d. purifying the ansamitocins by crystallization.

3. The method of claim 1 or 2 wherein the ansamitocin producing microorganism is Actinosynnema spp.

4. The method of claim 3 wherein the Actinosynnema spp. is *Actinosynnema pretiosum* ATCC 31565.

5. The method of claim 3 wherein the Actinosynnema spp. is *Actinosynnema pretiosum* ATCC 31281.

6. The method of claim 1 wherein the treatment is heating at about 75° C.

7. The method of claim 1 or 2 wherein the solvent is toluene.

8. The method of claim 7 wherein the ratio of toluene to heat-treated culture medium is about 1:1.

9. The method of claim 8 wherein the extraction is at about 45° C.

10. The method of claim 1 or 2 wherein the solvent is xylene.

11. The method of claim 10 wherein the ratio of xylene to heat-treated culture medium is about 1:1.

12. The method of claim 11 wherein the extraction is at about 45° C.

13. The method of claim 1 or 2 wherein the ansamitocins comprise acylated ansamitocins that can undergo reductive cleavage to form maytansinol.

* * * * *